Figure 3:
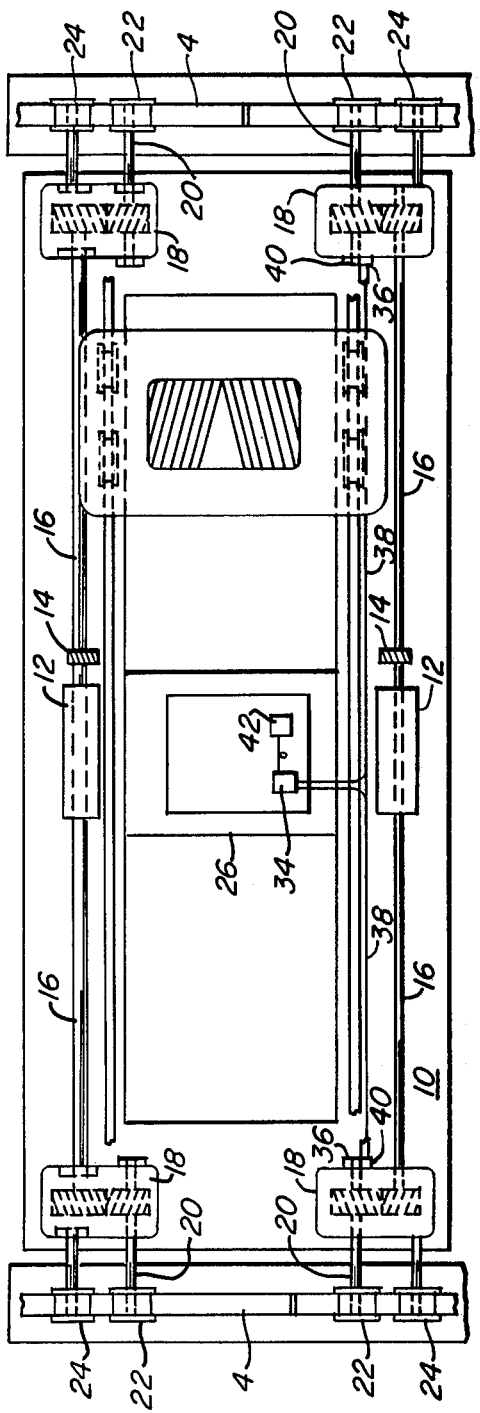

United States Patent [19]
McNeil

[11] 3,974,689
[45] Aug. 17, 1976

[54] SYSTEM FOR DETECTING FAULTS ALONG AN ELECTRIC OVERHEAD TRAVELING CRANE RUNWAY

[75] Inventor: Thomas Karl McNeil, Merrillville, Ind.

[73] Assignee: United States Steel Corporation, Pittsburgh, Pa.

[22] Filed: Mar. 11, 1975

[21] Appl. No.: 557,445

[52] U.S. Cl.................................. 73/146; 73/71.4
[51] Int. Cl.².......................................... G01M 19/00
[58] Field of Search ................ 73/71.4, 70, 67, 69, 73/146, 8; 33/144

[56] References Cited
UNITED STATES PATENTS
3,718,040   2/1973   Freeman et al...................... 73/146

Primary Examiner—James J. Gill
Assistant Examiner—Anthony V. Ciarlante
Attorney, Agent, or Firm—Rea C. Helm

[57] ABSTRACT

A system for the detection of faults along an electric overhead traveling crane runway has a transducer detecting axial movement of a crane wheel drive shaft connected to a vibration analyzer. As the crane is moved along the runway, the analyzer provides a signal indicative of axial vibrations to a calibrated recorder to produce a graphical record which is correlated with the location of supporting columns and rail joints.

14 Claims, 9 Drawing Figures

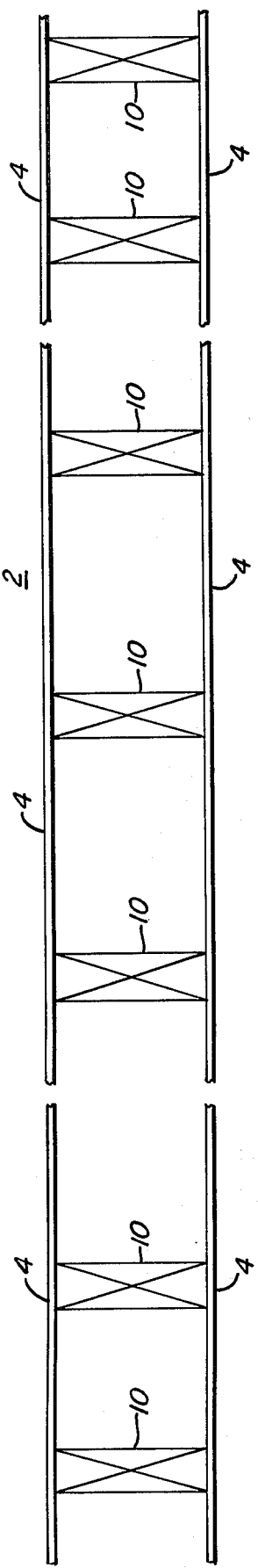
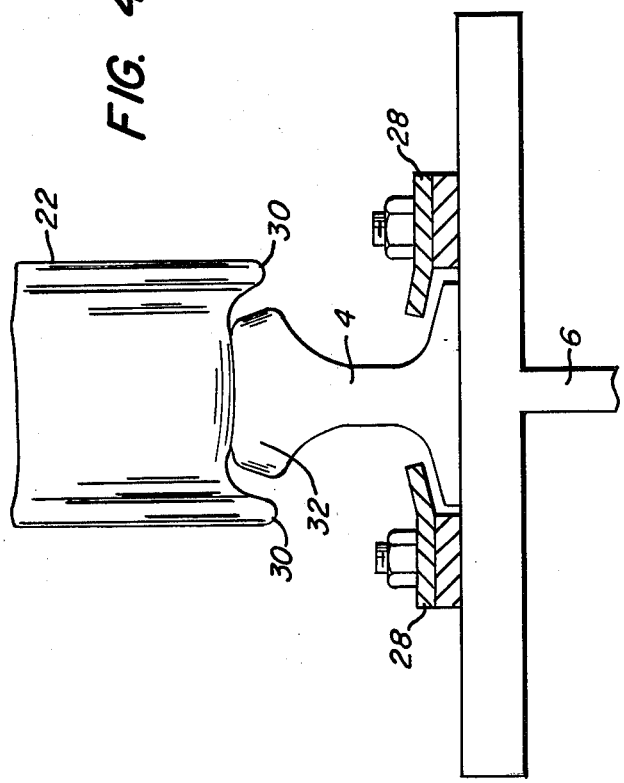
FIG. 1
FIG. 4

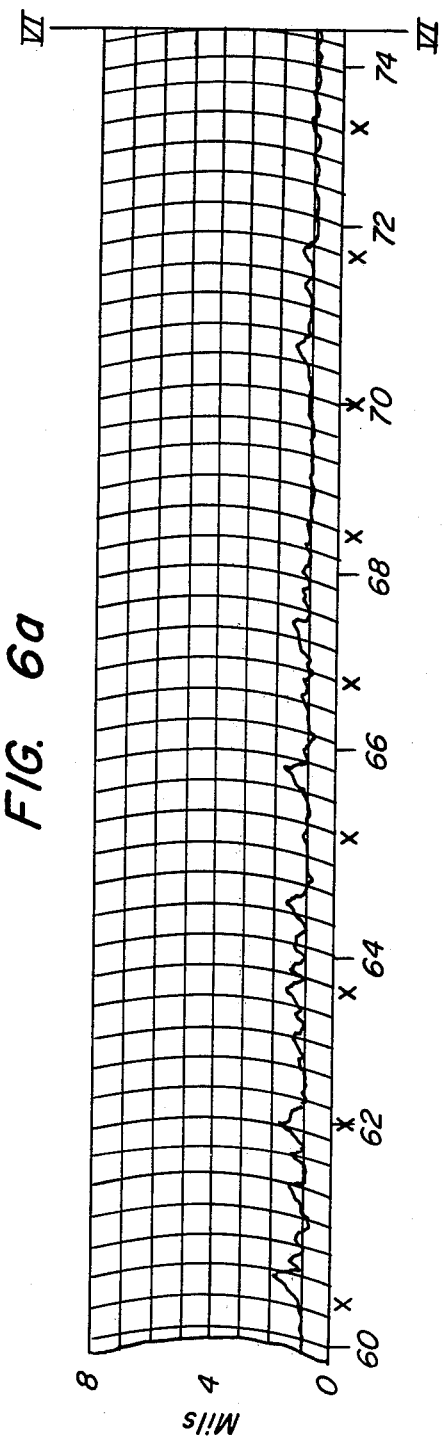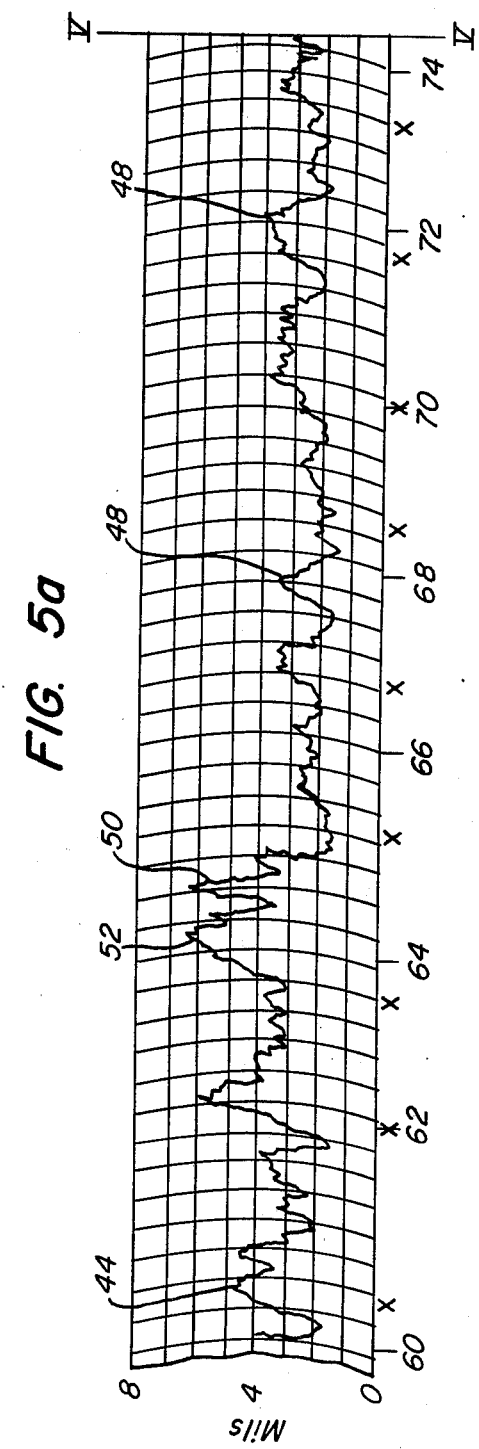

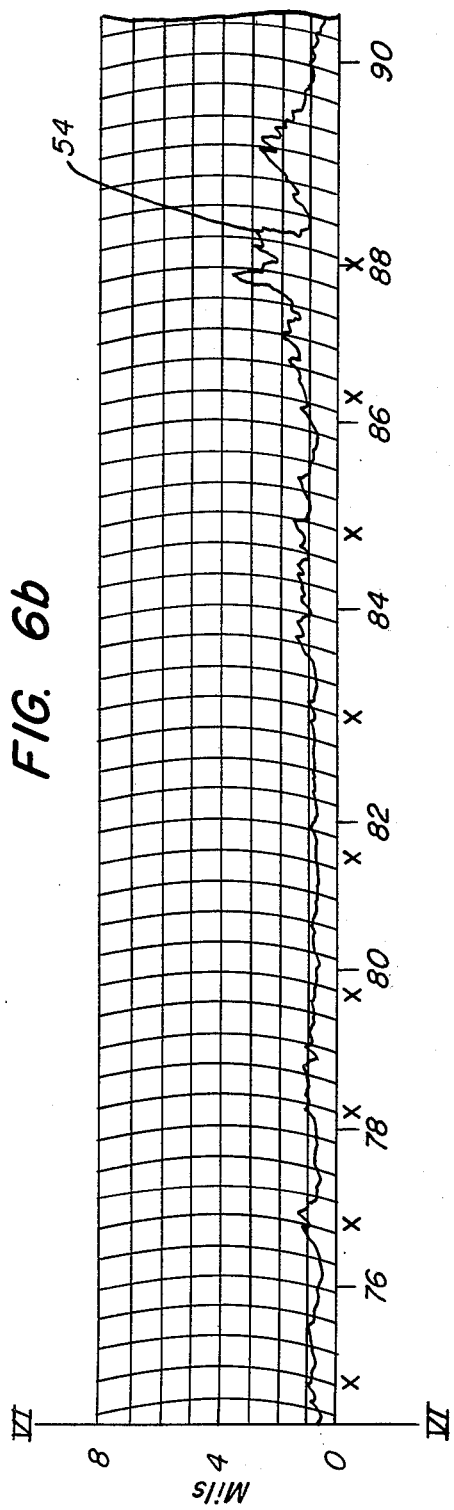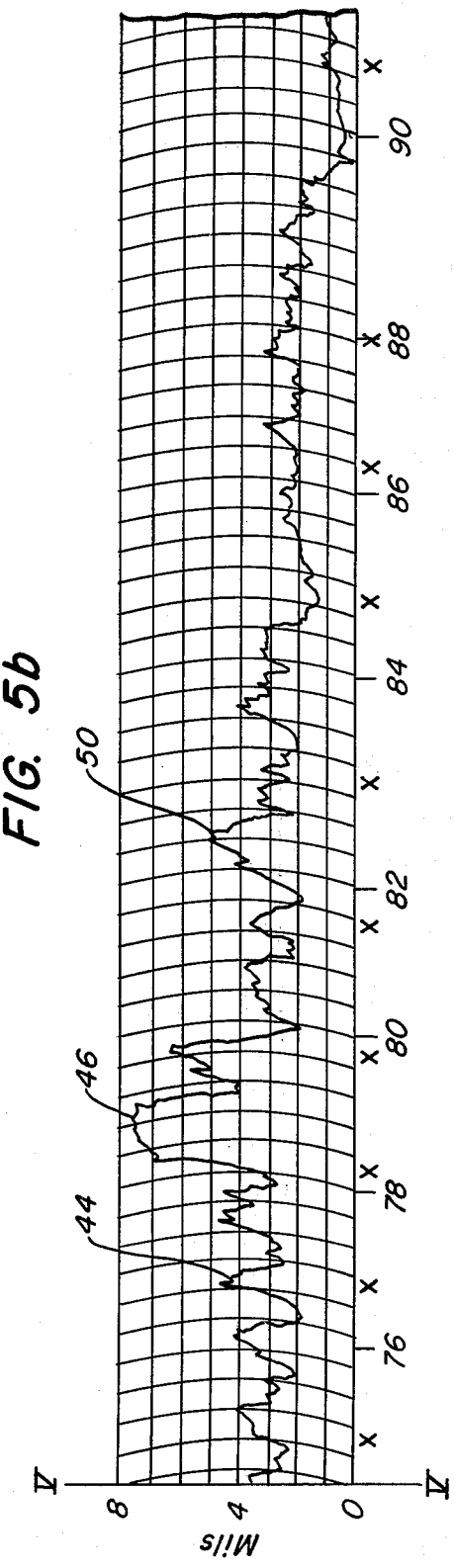

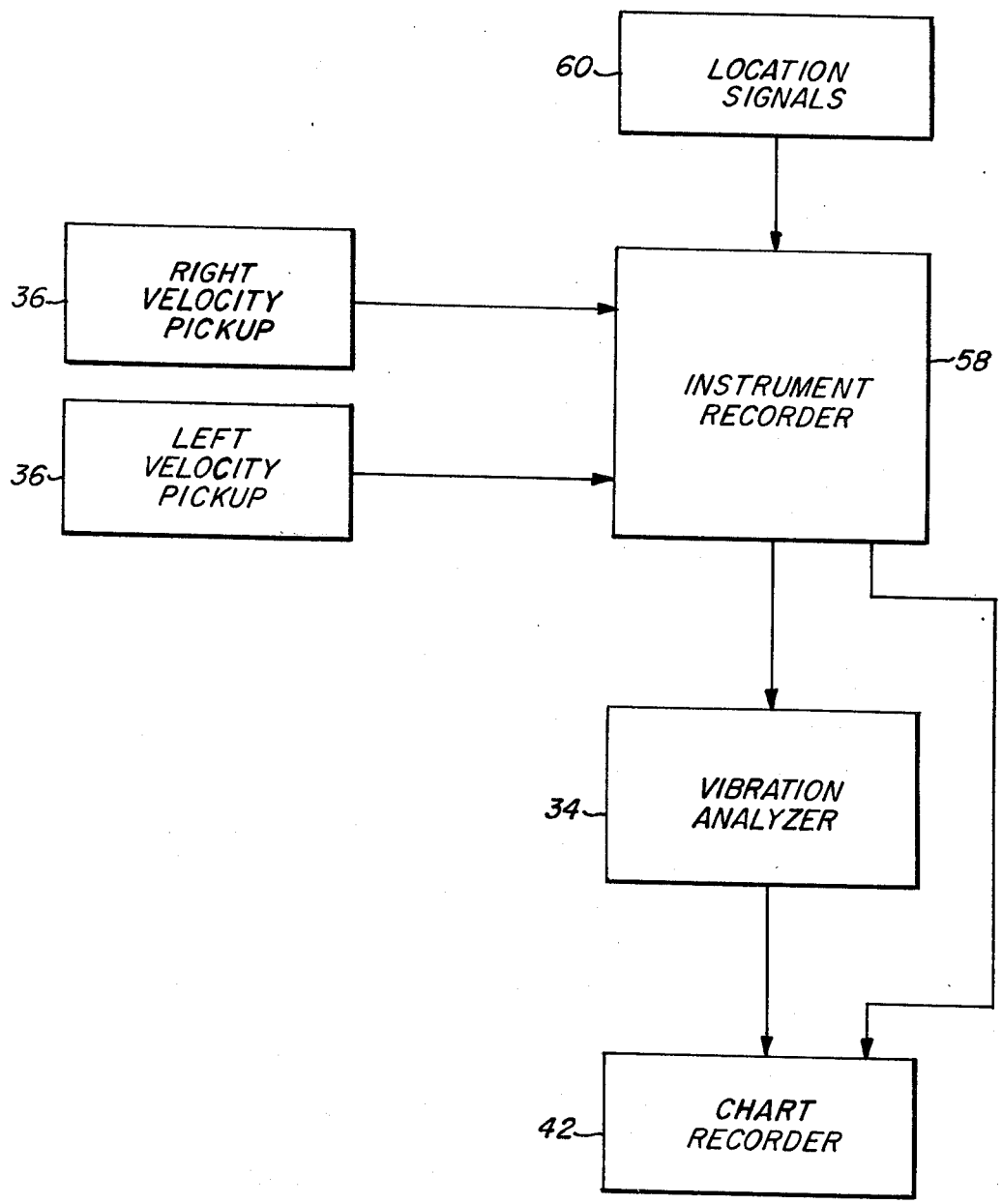

SYSTEM FOR DETECTING FAULTS ALONG AN ELECTRIC OVERHEAD TRAVELING CRANE RUNWAY

BACKGROUND OF THE INVENTION

This invention relates to the detection of faults along an electric overhead traveling crane runway and more particularly to a system for detecting the location of rail conditions that cause excessive wear of crane wheels and rails.

Excessive wear of the rails and wheels of electric overhead traveling cranes may be caused by a number of undesirable conditions such as settled supporting columns, poor rail splices or misaligned rails. Such defects are usually identified by detailed inspections of anchors, bolts, rail end joints and may also require careful measurements of rail spacing, elevation and alignment. Such inspections usually require a lengthy period when the crane or cranes must be out of service and often have questionable value since so much of the inspection is based on the judgement of the inspector. In addition, such inspections require walking the length of runways, a task requiring extreme care by the inspector. Once an inspection has been made and defects discovered and corrected, there is no simple method for determining whether the corrective efforts were completely satisfactory other than another more tedious inspection.

In accordance with my invention, axial vibrations of crane wheel drive shafts are detected and recorded graphically as the crane travels along the runway. The locations of the vibrations are graphically correlated with runway supporting column locations and rail splice locations and the locations where vibration amplitudes are greater than an acceptable level are an indication of the potential presence of an undesirable condition which may cause excessive wear. The test method is relatively simple, fast, repeatable and provides a permanent record. The location of the excessive vibration amplitudes also provides some direction in determining the nature of a particular condition causing the vibrations.

It is therefore an object of my invention to provide an accurate and fast method for determining the location of faults along an electric overhead traveling crane runway that cause wear on the crane wheels.

Another object is to provide apparatus for permanently recording the location and extent of such faults.

Figure 2:
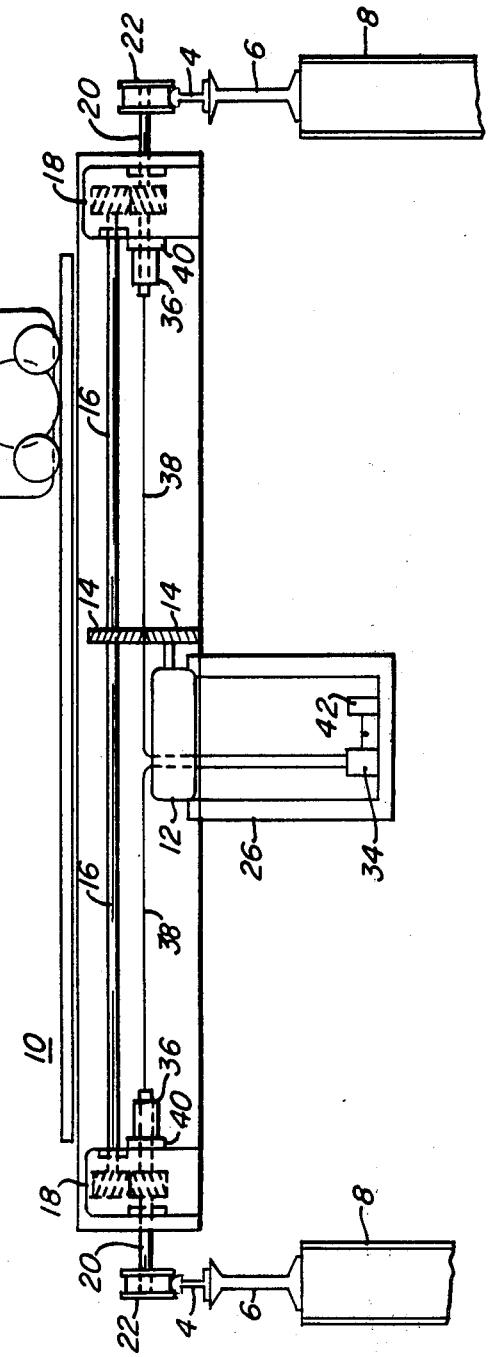

These and other objects will become more apparent after referring to the following drawings and specification in which FIG. 1 is a simple diagrammatic sketch of a crane installation where the system may be used, FIG. 2 is a diagrammatic elevational view of a crane showing the features of the invention, FIG. 3 is a diagrammatic plan view of a crane showing the features of the invention, FIG. 4 is a partial sectional view of a crane rail and wheel illustrating a floating rail, FIGS. 5a and 5b when joined along lines V—V is a graphic representation of a test run using the method of my invention, FIGS. 6a and 6b when joined along lines VI—VI is a graphic representation of a test run along the same runway as FIG. 5 but after corrective action, and FIG. 7 is a block diagram showing the components of an alternative embodiment of my invention.

Referring now to the drawings, and particularly to FIGS. 1, 2, 3 and 4, reference numeral 2 (FIG. 1) refers to a long crane runway to which my invention is particularly adapted. Runway 2 consists of a pair of crane rails 4 each supported on a supporting beam 6 which is in turn supported by a series of columns 8, two of which are partially shown in FIG. 2. One or more electric overhead cranes 10 travel along runway 2. As shown in FIG. 1, a particular installation has seven cranes operating on a single runway about 2400 feet long. Each crane 10, (FIGS. 2 and 3) includes a bridge drive motor 12 connected through gears 14, shafts 16, gear boxes 18 and drive shafts 20 to drive wheels 22. There may be additional support wheels 24. Each crane also includes a control cab 26. In FIG. 4, a part of a wheel 22 is shown resting on rail 4. Rail 4 is attached to beam 6 by clamps 28 so that rail 4 may move slightly in a lateral direction sometimes called a floating rail. Wheels 22 typically are double flanged 30 and are designed to be spaced away from rail head 32. The parts thus far described represent a conventional electric overhead traveling crane installation to which my invention is applicable.

In accordance with my invention, a vibration analyzer 34 (FIGS. 2 and 3) is placed in a convenient location in cab 26. Analyzer 34 may be an IRD Mechanalysis Vibration Analyzer - Dynamic Balancer Model No. 600 as manufactured by IRD Mechanalysis, Inc., 6150 Huntley Road, Columbus, Ohio. Analyzer 34 is connected to a velocity pickup 36 by a cable 38. As shown, there is a right hand pickup and left hand pickup, but a single pickup and cable may be used in one location and then moved to the other location. Velocity pickup 36 is a part of analyzer 34 and is the type of transducer in which movement along its longitudinal axis results in a voltage signal output proportional to the relative velocity between a coil and a magnetic field in the transducer. Pickup 36 is unidirectional and is magnetically attached to bearing cover 40 of gear box 18 in a position to detect axial movement of shaft 20. A chart recorder 42 is connected to analyzer 34 and may be conveniently located in cab 26 with analyzer 34. Recorder 42 may be a Brush Recorder Mark II manufactured by Brush Instrument Division, 37th and Perkins, Cleveland, Ohio.

In the practice of my invention, velocity pickup 36 is placed on the gear box bearing cover 40 in a position so that axial vibration or movement of drive shaft 20 will provide the signals to the analyzer. While other alignments could also be used to detect vibrations, I prefer to use axial alignment because it provides an indication of all faults within a desirable response range. For example, a vertically oriented pickup would readily detect differences in rail head elevation at a faulty splice joint, but the magnitude of the signal becomes so large that it may obscure another nearby fault arising from a different cause. The axial alignment then measures any misalignment as a thrust on the bearings reacting from flanges 30 rubbing on the sides of rail 4.

Analyzer 34 amplifies the signal from pickup 36 to a level required to drive recorder 42 and has the capability of calibrating recorder 42 to indicate actual displacement of bearing cover 40. In the preferred embodiment, I have found that a particular crane bearing cover may be displaced as much as 8 mils during a test run, and that background vibrations caused by movement of other cranes on the same runway during a test run, as well as from any other causes, may be as high as 3 mils. Accordingly, it is desirable to record a maximum of 8 mils on the recorder, and the recorder and analyzer are adjusted so that each square on the chart width illustrated in FIGS. 5 and 6 represents one mil displacement of bearing cover 40.

With the analyzer and recorder calibrated the chart speed is set to provide a readable output at the expected crane speed. For example, at a crane speed of about 8 feet per second, a chart speed of 5 mm per second provides a very readable chart. The charts shown in FIGS. 5 and 6 were made at about these speeds.

The crane is then ready for operation over the length of the runway which is to be tested while the recorder continuously records the analyzer output signal as a measure of the displacement of bearing cover 40. A fixed speed should be used so that the test may be repeatable. Both right and left hand rails may be tested simultaneously or separate runs may be used for each side.

Referring now to FIGS. 5a and 5b which is a reproduction of an actual test chart, the reference numerals along the bottom refer to column numbers along the section of runway being tested, beginning at column number 90 and ending at column number 60. As the crane moves along the runway during a test, an operator visually observes column locations and places a small vertical mark on the recording location of the chart as the crane passes each column. Since column spacings are known, rail splice locations can then be measured as distances from column locations and then each marked with an X on the chart.

As the crane passes over a worn rail splice, the shock from the impact between the rail and the wheel excites the pickup and results in an increase in the analyzer output. The severity of the rail wear is proportional to the shock which is proportional to the amplitude of the recording. Reference numerals 44 indicate potential faulty rail joints because of the amplitude of recording at the rail joints.

If the crane passes over an area where there is rail misalignment, a high level of vibration will occur over a relatively long period of time as shown at 46. This may result from a bowed section of rail 4 or the rail may not be floating under load, see FIG. 4. When such conditions occur, wheel flanges 30 rub against the head of rail 4 which creates excessive vibrations over that section of rail. Other spikes on the recording such as at 48 may indicate potentially settled supporting columns because of their location on the chart with respect to supporting columns. Other high amplitude recordings such as at 50 indicate the need for supplemental visual inspection of the crane runway in the particular locations. Recordings such as at 52 indicate a need to check for problems on the opposite rail at that location.

The recordings of FIG. 5 indicate that vibrations were recorded within a general amplitude range of 3 to 8 mils. In FIGS. 6a and 6b, a recording made after the recording of FIG. 5 but with the runway defects corrected and new wheels installed on the crane, the vibrations were recorded at a much lower level, and only a single rail joint at 54 was found that could possibly be considered as unsatisfactory.

FIG. 7 illustrates a different way of developing and recording test information. One or two velocity pickups 36 are connected to a multi-channel instrument tape recorder 58 which includes input signal arrangements 60 to record signals indicating column locations and rail joint locations if desired. The tape may then be later connected to the vibration analyzer 34 and chart recorder 42 at a more convenient location than the crane cab 26 for recording purposes.

This system provides a safe, accurate and simple method for determining runway faults and provides a permanent record of the test run.

While several embodiments of my invention have been shown and described, it will be apparent that other adaptations and modifications may be made without departing from the scope of the following claims.

I claim:

1. A method of detecting faults along an electric overhead traveling crane runway comprising the steps of
    moving the crane along the runway,
    detecting axial movement of a crane wheel drive shaft as the crane moves along the runway,
    converting the detected movement into an electrical signal having an amplitude corresponding to the magnitude of the movement,
    recording graphically the amplitude of the electrical signal as the crane moves along the runway, and
    recording on the graphical representation of the electrical signal a plurality of longitudinal runway locations correlated with the electrical signal derived from detected movement at each such location.

2. A method according to claim 1 in which the longitudinal runway locations are runway supporting column locations.

3. A method according to claim 2 in which the longitudinal runway locations also includes runway rail joint locations.

4. A method according to claim 3 in which the movement is detected with the use of a transducer mounted on a drive shaft bearing cover.

5. A method according to claim 4 which includes calibrating the graphical representation of the electrical signal to indicate the actual displacement of the bearing cover.

6. A method of detecting faults along an electric overhead traveling crane runway comprising the steps of
    moving the crane along the runway,
    detecting axial movement of a crane wheel drive shaft as the crane moves along the runway,
    converting the detected movement into an electrical signal having an amplitude corresponding to the magnitude of the movement,
    recording on a multi-channel recorder the electrical signal and a plurality of longitudinal runway location signals correlated with the electrical signal derived from detected movement at each such location and
    providing a graphical representation of the electrical signal and the correlated location signals from a playback of the recording.

7. A method according to claim 6 in which the longitudinal runway locations are runway supporting column locations.

8. A method according to claim 7 in which the longitudinal runway locations also include runway rail joint locations.

9. A method according to claim 8 in which the movement is detected with the use of a transducer mounted on a drive shaft bearing cover.

10. A method according to claim 9 which includes calibrating the graphical representation of the electrical signal to indicate the actual displacement of the bearing cover.

11. Apparatus for detecting faults along an electric overhead traveling crane runway comprising
means mounted on the crane for detecting axial movement of a crane wheel drive shaft and providing an electrical signal having an amplitude corresponding to the magnitude of the movement as the crane moves along the runway,
means connected to the means for providing a signal for amplifying the electrical signal and
means connected to said amplifying means for providing a graphical representation of the amplitude of the electrical signal along the crane runway.

12. Apparatus according to claim 11 in which the means for amplifying the electrical signal includes means for changing said signal whereby the graphical representation of amplitude is calibrated to indicate actual magnitude of the movement.

13. Apparatus for detecting faults along an electric overhead traveling crane runway comprising
means mounted on the crane for detecting axial movement of a crane wheel drive shaft and providing an electrical signal having an amplitude corresponding to the magnitude of the movement as the crane moves along the runway,
a multi-channel recorder connected to said detecting means for recording the amplitude of the electrical signal on one channel,
means connected to said recorder for recording a plurality of longitudinal runway location signals correlated with the electrical signal derived from detected movement at each such location on another channel and
means connected to said recorder for providing a graphical representation of the electrical signal and correlated location signals.

14. Apparatus according to claim 13 which includes means connected between the means for recording and the means for providing the graphical representation for amplifying said electrical signal and changing said signal whereby the graphical representation of amplitude is calibrated to indicate actual magnitude of the movement.

\* \* \* \* \*